US008367045B2

(12) United States Patent
Raney et al.

(10) Patent No.: US 8,367,045 B2
(45) Date of Patent: Feb. 5, 2013

(54) METHOD OF PREPARATION OF RADIATION-CURABLE COLORED ARTIFICIAL NAIL GELS

(75) Inventors: Robert R. Raney, Newtown Square, PA (US); Kevin M. Sheran, Philadelphia, PA (US); Larry W. Steffier, Cherry Hill, NJ (US); Gary Iannece, Bordentown, NJ (US)

(73) Assignee: Mycone Dental Supply Co., Inc., Cherry Hill, NJ (US)

( * ) Notice: Subject to any disclaimer, the term of this patent is extended or adjusted under 35 U.S.C. 154(b) by 0 days.

(21) Appl. No.: 13/232,618

(22) Filed: Sep. 14, 2011

(65) Prior Publication Data

US 2012/0004340 A1 Jan. 5, 2012

Related U.S. Application Data

(63) Continuation-in-part of application No. 12/725,073, filed on Mar. 16, 2010, now abandoned.

(51) Int. Cl.
C08L 1/00 (2006.01)
C08L 33/06 (2006.01)
C08J 3/20 (2006.01)
C08J 3/28 (2006.01)
A45D 31/00 (2006.01)
A61Q 3/02 (2006.01)

(52) U.S. Cl. ............. 424/61; 424/401; 522/79; 522/80; 522/83; 522/88; 522/89; 522/173; 522/182

(58) Field of Classification Search .................. 522/79, 522/83, 80, 173, 182, 78; 424/61, 401
See application file for complete search history.

(56) References Cited

U.S. PATENT DOCUMENTS

| | | | |
|---|---|---|---|
| 4,649,045 A | 3/1987 | Gaske et al. | |
| 4,682,612 A | 7/1987 | Giuliano | |
| 5,133,966 A | 7/1992 | Khamis | |
| 5,830,442 A | 11/1998 | Beaver | |
| 5,882,636 A | 3/1999 | Mui et al. | |
| 5,965,147 A | 10/1999 | Steffier | |
| 5,985,951 A | 11/1999 | Cook | |
| 6,051,242 A | 4/2000 | Patel et al. | |
| 6,270,751 B1 | 8/2001 | Resler | |
| 6,455,033 B1* | 9/2002 | Steffier | 424/61 |
| 6,537,530 B2 | 3/2003 | Mui et al. | |
| 6,616,920 B1 | 9/2003 | Ito et al. | |
| 6,803,394 B2 | 10/2004 | Lilley et al. | |
| 6,998,425 B2* | 2/2006 | Chisholm et al. | 522/182 |
| 8,263,677 B2* | 9/2012 | Conger et al. | 522/182 |
| 2003/0175347 A1* | 9/2003 | Steffier et al. | 424/468 |
| 2005/0065297 A1 | 3/2005 | Patel | |
| 2006/0283720 A1 | 12/2006 | Minnella | |
| 2008/0241083 A1 | 10/2008 | Schoon et al. | |
| 2010/0008876 A1 | 1/2010 | Tanaka et al. | |
| 2011/0256080 A1* | 10/2011 | Kozachek et al. | 424/61 |

OTHER PUBLICATIONS

International Preliminary Report on Patentablibility mailed on Sep. 5, 2012 by KIPO including Demand under Article 34 filed Feb. 23, 2012.

* cited by examiner

*Primary Examiner* — Susan W Berman
(74) *Attorney, Agent, or Firm* — Eckert Seamans Cherin & Mellott, LLC; Michael B. Fein

(57) ABSTRACT

A method of preparing colored UV-curable artificial nail gel compositions comprising dispersing a pigment in an organic liquid to form a pigment concentrate and mixing the pigment concentrate with a polyfunctional acrylic monomer and/or a polyfunctional acrylic oligomer, and the resultant highly colored artificial nail gel are disclosed.

19 Claims, No Drawings

METHOD OF PREPARATION OF RADIATION-CURABLE COLORED ARTIFICIAL NAIL GELS

CROSS-REFERENCE TO RELATED APPLICATIONS

Benefit of U.S. Non-Provisional application Ser. No. 12/725,073, filed Mar. 16, 1010 now abandoned, is claimed.

BACKGROUND OF THE INVENTION

This invention relates to the field of radiation-curable gels useful for cosmetic adornment of natural nails, artificial fingernails, toenails and artificial nail extensions.

The use of radiation-curable gels in formation of nail enhancements or artificial nails has been an important part of the cosmetic industry since it was first introduced. U.S. Pat. No. 4,682,612, describing the use of actinic radiation-curable compositions suitable for preparation of artificial nails, is representative of this technology.

Ultra-violet radiation (UV) is the most conventional form of radiation used to cure gels in this art, however, visible light curing systems are also known. UV-curable gels are most typically applied by professional nail technicians. Such UV-curable gels are usually composed of acrylic or methacrylic monomers and oligomers in a gel-like state that requires curing under a UV lamp. Such nail finishes can be applied directly to natural fingernails or toenails, or alternatively can be applied to nail extensions bonded to fingernails. In many cases, the artificial nails are coated with conventional nail polish after they are cured.

In order to avoid the need to coat the artificial nails or natural nails with conventional nail polish, in more recent years, the preparation of gels containing colorants, particularly pigments, has become known in this art. However, the previously suggested processes used to prepare such colored gels have several disadvantages. One such process, the direct of addition of pigment powders, is described in US Pat. Pubs. US2006/0283720 and US2010/0008876. The direct use of pigment powders brings with it the disadvantages of difficulty in handling, inconsistent dispersion leading to poor color control, the need for high shear mixing or milling full batches of material, and the need for expensive large scale equipment. The direct mixing of all components including pigment powders in a suitable solvent is described in U.S. Pat. No. 5,985,951 which brings the same disadvantages. As an alternative to incorporating pigments per se, a gel composition combined with commercial nail polish is described in U.S. Pat. No. 6,803,394. In this patent, commercial nail polish is added to a UV-curable artificial nail gel by the applicator as a means for coloring the gel and resultant artificial nails.

The use of commercial nail polish is undesirable in that it limits the depth of color that can be achieved in a given coating weight. Thus, compared to the commercial nail polish itself, a lower color density will be achieved and attempts to increase the amount of nail polish will lead to systems which give poor curing characteristics or discomfort due to the thick coating required to provide the desired color depth.

It has been a long felt need in this art to provide integrally colored artificial nails which have a reproducible, predictable color when cured.

There is also a need for an improved method to produce color containing UV-curable gels which give high color density.

There is also a need for an alternative to directly adding pigments to artificial nail gels to avoid the requirement of applying high shear to the gels in order to effectively incorporate the pigments.

SUMMARY OF THE INVENTION

These objectives, and others as will become apparent from the following description, are achieved by the present invention which comprises in one aspect a method for preparing high color density gels without the use of high shear by introducing the pigment in the form of a homogeneously pre-dispersed concentrate.

In another aspect, the invention comprises a highly colored UV-curable artificial nail gel prepared by such method.

DETAILED DESCRIPTION OF PREFERRED EMBODIMENTS

According to the invention, high density color gels can be successfully prepared using flowable pigment concentrates without the use of high shear in the production of the final gel. The concentrates can be added to gel formulations including commercially available nail gels without the use of high shear conditions to give suitable colored gels for nails.

The UV-curable artificial nail gels can comprise a wide variety of compounds containing one or more radical polymerizable unsaturated double bond. Typical examples include esters of acrylic and methacrylic acid, herein termed (meth)acrylic ester. Specific but not limiting examples of mono (meth)acryloyl esters include methyl (meth)acrylate, ethyl (meth)acrylate hydroxypropyl (meth)acrylate, ethyl (meth)acrylate , butyl (meth)acrylates, hydroxy ethyl (meth)acrylates, butoxyethyl (meth)acrylate, diethylaminoethyl (meth)acrylate, 2-ethylhexyl (meth)acrylate, ethoxyethyl (meth)acrylate, t-butyl aminoethyl (meth)acrylate, methoxyethylene glycol (meth)acrylate, phosphoethyl (meth)acrylate, methoxy propyl (meth)acrylate, methoxy polyethylene glycol(meth)acrylate, phenoxyethylene glycol (meth)acrylate, phenoxypolyethylene glycol (meth)acrylate, 2-hydroxy-3-phenoxypropyl (meth)acrylate, 2-(meth)acryloxyethylsuccinic acid, 2-(meth)acryloylethylphthalic acid, 2-(meth)acryloyloxypropylphthalic acid, stearyl (meth)acrylate, isobornyl (meth)acrylate, 3-chloro-2-hydroxypropyl (meth)acrylates, tetrahydrofufuryl (meth)acrylate, (meth)acrylamides and allyl monomers. Specific but not limiting examples of difunctional methacryloyl esters include 1,4 butane diol di(meth)acrylate, 1,6 hexanediol di(meth)acrylate, 1,9 nonanediol di(meth)acrylate, 1,10 decanediol di(meth)acrylate, neopentyl glycol di(meth)acrylate, 2-methyl-1,8-octane diol di(meth)acrylate, glycerin di(meth)acrylate, ethylene glycol di(meth)acrylate, triethylenglycol di(meth)acrylate, polyethylene glycol di(meth)acrylate, propylene glycol di(meth)acrylate, polypropylene glycol di(meth)acrylate, ethoxylated propylene glycol di(meth)acrylate, ethoxylated polypropylene glycol di(meth)acrylate, polyethoxypropoxy di(meth)acrylate, ethoxylated bisphenol A di(meth)acrylate, propoxylated bisphenol A di(meth)acrylate, propoxylated ethoxylated bisphenol A di(meth)acrylate, bisphenol-A glycidyl dimethacrylate, tricyclodecanedimethanol di(meth)acrylate, glycerin di(meth)acrylate, ethoxylated glycerin di(meth)acrylate, bis acrylamides, bis allyl ethers and allyl (meth)acrylates. Examples of in and or higher (meth)acryloyl esters include trimethylol propane tri(meth)acrylate, ethoxylated glycerin tri(meth)acrylate, ethoxylated trimethylolpropane tri(meth)acrylate, ditrimethylol propane tetra(meth)acrylate, pentaerythritol tri(meth)acrylate, pentaerythritol tetra(meth)acrylate, propoxylated pentaerythritol tetra(meth)acrylate, ethoxylated pentaerythritol tetra(meth)acrylate, dipentaerythritol hexa(meth)acrylate, and ethoxylated isocyanuric acid tri(meth)acrylates.

Urethane(meth)acrylates, useful in the present invention, have at least two or more acryloyl or methacryloyl groups and a urethane group. Examples include urethanes based on aliphatic, aromatic, polyester, and polyether polyols and aliphatic, aromatic, polyester, and polyether diisocyanates capped with (meth)acrylate endgroups. Isocyanate prepolymers can also be used in place of the polyol/diisocyanate core. Epoxy (meth)acrylates and epoxy urethane (meth)acrylates, useful in the present invention, have at least two or more acryloyl or methacryloyl groups and, optionally, a urethane group. Examples include epoxy (meth)acrylates based on aliphatic or aromatic epoxy prepolymers capped with (meth)acrylate endgroups. A aliphatic or aromatic urethane spacer can be optionally inserted between the epoxy and the (meth)acrylate endgroup(s). Acrylated polyester oligomers, useful in the present invention, have at least two or more acryloyl or methacryloyl groups and a polyester core. Acrylated polyether oligomers, useful in the present invention, have at least two or more acryloyl or methacryloyl groups and a polyether core. Acrylated acrylate oligomers, useful in the present invention, have at least two or more acryloyl or methacryloyl groups and a polyacrylic core. These reactive urethanes, epoxies, polyesters, polyethers and acrylics are available from several suppliers including BASF Corporation, Bayer MaterialScience, Bomar Specialties Co, Cognis Corporation, Cytec Industries Inc, DSM NeoResins, Eternal Chemical Co, Ltd, IGM Resins, Rahn AG, Sartomer USA, LLC, and SI Group, Inc.

In addition to the above-described (meth)acrylate-based polymerizable monomers, other polymerizable monomers, oligomers or polymers of monomers which contain at least one free radical polymerizable group in the molecule may be used without any limitations in the curable gel. These monomers may contain an acidic group to improve adhesion.

A compound having at least one free radical polymerizable group includes not only a single component but also a mixture of polymerizable monomers. Thus combinations of two or more materials containing free radical polymerizable groups may be used in combination.

The gels also contain a photoinitiator. Examples of these include include benzyl ketones, monomeric hydroxyl ketones, polymeric hydroxyl ketones, .alpha.-amino ketones, acyl phosphine oxides, metallocenes, benzophenone, benzophenone derivatives, and the like. Specific examples include 1-hydroxy-cyclohexylphenylketone, benzophenone, 2-benzyl-2-(dimethylamino)-1-(4-(4-morphorlinyl)phenyl)-1-butanone, 2-methyl-1-(4-methylthio)phenyl-2-(4-morphorlinyl)-1-propanone, diphenyl-(2,4,6-trimethylbenzoyl) phosphine oxide, phenyl bis(2,4,6-trimethylbenzoyl) phosphine oxide, benzyl-dimethylketal, isopropylthioxanthone, and mixtures thereof.

Photo accelerators such as aliphatic or aromatic amines may also be included in the gel as well as fillers, inhibitors, plasticizers, non-reactive polymers, and adhesion promoters.

By the term "gel," we mean a radiation-curable composition comprising photoinitiator, ethylenically unsaturated monomers and/or oligomers, having a viscosity suitable for coating natural or artificial nails, or forming artificial nails and extensions, as well as adorning such nails.

A different viscosity range is preferred for each of these applications. Typical viscosities can range widely, from 2 to 500 poise, depending on the application. For building artificial nails, viscosities between 20 and 500 poise are commercially available. For coatings, less than 25 poise is typical.

There are many possible embodiments of the gel. In some embodiments the gel is comprised of 70-80% by weight an aliphatic polyester based urethane diacrylate oligomer, 20-30% by weight glycol HEMA-methacrylate (ethylene glycol dimethacrylate), 3-5% by weight hydroxycyclohexyl phenyl ketone, and 3-5% by weight benzophenone. In certain other embodiments the gel is comprised of 60-70% by weight an aliphatic polyester based urethane diacrylate oligomer, 5-10% by weight 2-hydroxyethyl methacrylate (HEMA), 5-10% by weight isobornyl methacrylate, and up to 1% by weight hydroxycyclohexyl phenyl ketone. Another embodiment of the gel is comprised of 50-60% by weight an aliphatic polyester based urethane diacrylate oligomer, 15-20% by weight HEMA, 15-20% by weight hydroxypropyl methacrylate, and up to 1% by weight hydroxycyclohexyl phenyl ketone.

The pigment concentrates which are used in the invention generally contain 10-50% pigment which may be dispersed in an organic liquid comprised of one or more chemicals selected from solvents, ethylenically unsaturated monomers, and ethylenically unsaturated oligomers. The organic liquid may also comprise non-reactive polymer, filler, and dispersant. For example, the organic liquid may comprise as non-reactive polymers nitrocellulose, cellulose acetate propionate, cellulose acetate butyrate, and similar cellulose-based polymers and other synthetic non-reactive polymers, with or without solvent. The organic liquid has one continuous phase whereas the pigment is a discontinuous phase of the pigment concentrate. Examples of suitable solvents are butyl acetate, ethyl acetate, isopropanol, xylene, toluene, acetone, and methyl ethyl ketone. Examples of ethylenically unsaturated monomers are (meth)acrylic esters, and examples of ethylenically unsaturated oligomers are urethane (meth)acrylates. The concentrates may be dispersed in the same UV-curable monomers and/or oligomers as used in the gel formulation by any means, for example by shearing of the pigment directly into the organic liquid. In one embodiment the organic liquid in which the pigment is dispersed comprises ethyl acetate, butyl acetate, and nitrocellulose. In another embodiment the organic liquid also comprises a solvent.

Suitable pigments which can be incorporated into the concentrates include barium, calcium and aluminum lakes, iron oxides, chromates, molybdates, cadmiums, metallic or mixed metallic oxides, talcs, carmine, titanium dioxide, chromium hydroxides, ferric ferrocyanide, ultramarines, titanium dioxide coated mica platelets, and/or bismuth oxychlorides, Preferred pigments include D&C Black No. 2, D&C Black No. 3., FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4., D&C Red No. 6, D&C Red No. 7, D&C Red No. 17, D&C Red No. 21, D&C Red No. 22, D&C Red No. 27, D&C Red No. 28, D&C Red No. 30. D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, as well as others listed on the FDA color additives website, and Annex IV of the Cosmetic Directive 76/768/EEC, Coloring Agents Permitted in Cosmetics.

These pigments are homogenously dispersed into the concentrate and then the concentrate is incorporated into the final gel product by blending without the need for high shear processing. The ratio of pigment concentrate to gel composition is preferably equal to or less than 1:2.

The use of high color pigment content in these final gels (>0.4 pph) can reduce the ability to cure thick films and thus thinner coats of the resulting gel are preferred. To accomplish this, gels with lower viscosity than those typically used as builder gels are preferred, however high viscosity gels can also be used. Lower viscosity gels are preferred since their application properties are similar to standard nail polishes. Gel viscosities as measured at 25° C., ½ sec shear, on a TA Instruments AR500 Rheometer of around 3000 poise are considered high viscosities whereas gel viscosities of <25 poise are preferred.

In some embodiments the pigment concentrate can be sold separately from the gel so that the consumer or nail technician can mix them together before application.

EXAMPLES

Example 1

To 49.6 grams of UV-curable gel comprised of 58% by weight an aliphatic polyester based urethane diacrylate oligomer, 20% by weight hydroxyethyl methacrylate, 20% by weight hydroxypropyl methacrylate, and 2% by weight hydroxycyclohexyl phenyl ketone was added sequentially, with hand stirring, three pigment concentrate pastes. Each pigment concentrate paste was a dispersion of pigment in an organic liquid composed of butyl acetate solvent (30.0%-40.0%), ethyl acetate solvent (20.0%-30.0%), nitrocellulose (10.0%-20.0%), and isopropyl alcohol solvent 1.0%-5.0%. The pigments were $TiO_2$, D&C Red #6, and D&C Red #7 Light, and the amounts of dispersion added were 0.1, 5.9, and 2.8 grams, respectively.

Comparative Example 1

To 12.1 grams of the same UV-curable gel described in Example 1 were added 6 grams of OPI Big Apple Red Nail Polish with hand stirring.

In order to test whether the method of the invention was successful in matching the color and color density of the nail polish itself, the mixtures from Example 1, Comparative Example 1 and OPI Big Apple Red nail polish were each coated on 25 mm×75 mm slides to give a 1 inch×25 mm square. Different numbers of coats and coating weights were used. Coatings made with Example 1 and Comparative Example 1 were cured under UV lights for three minutes prior to applying a subsequent coat and again after the final coat. The nail polish example was dried for 30 min in between coats. A group of experts were then asked to rate the samples according to color density. Table 1 gives the results.

The ratings demonstrate that color density is significantly lower at any given number of coats or coating weight using the method of Comparative Example 1 as compared to Example 1. Significantly thicker coats of the comparative example were required in order to match either the initial nail polish color or the mixture from Example 1. Thus, an improved artificial nail gel material can be made from the method of the invention compared to that made via the comparative method.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. A method of preparing colored ultraviolet (UV)-curable compositions useful for adornment of natural and artificial nails and artificial nail extensions comprising dispersing a pigment in an organic liquid to form a pigment concentrate, the organic liquid comprised of one or more organic chemicals selected from solvents, ethylenically unsaturated monomers, and ethylenically unsaturated oligomers; and mixing the dispersed pigment concentrate with a radiation-curable nail gel composition consisting essentially of one or more ethylenically unsaturated monomers, one or more ethylenically unsaturated oligomers, or mixtures thereof, a photoinitiator and, optionally, one or more photo accelerators, fillers, inhibitors, plasticizers, non-reactive polymers, and adhesion promotors; the resultant mixture adapted to be curable in the presence of UV radiation.

2. The method of claim 1 wherein organic liquid is a non-reactive solvent.

3. The method of claim 1 wherein organic liquid comprises one or more non-reactive solvents selected from butyl acetate, ethyl acetate, isopropanol, xylene, toluene, acetone, and methyl ethyl ketone.

4. The method of claim 1 wherein organic liquid comprises one or more chemicals selected from mono-, di-, tri-, and tetra-functional ethylenically unsaturated monomers and oligomers.

TABLE 1

|  | Comparative Example 1 Number Of Coats/Coating Weight (mg) | | | | OPI Big Apple Red Nail Polish Number Of Coats/ Coating Weight (mg) | | Example 1 Number Of Coats/ Coating Weight (mg) | | |
|---|---|---|---|---|---|---|---|---|---|
|  | 1/69 | 1/107 | 2/172 | 3/255 | 4/320 | 1/71 | 2/141 | 1/68 | 1/82 | 2/147 |
|  | | | | | | Rating* | | | | |
| Rater 1 | 1 | 2 | 3 | 5 | 8 | 4 | 9 | 7 | 6 | 10 |
| Rater 2 | 1 | 2 | 3 | 5 | 8 | 4 | 9 | 6 | 7 | 10 |
| Rater 3 | 1 | 2 | 3 | 6 | 8 | 4 | 9 | 5 | 7 | 10 |
| Rater 4 | 1 | 2 | 3 | 5 | 7 | 4 | 10 | 6 | 8 | 9 |
| Rater 5 | 1 | 2 | 3 | 7 | 8 | 4 | 9 | 5 | 6 | 10 |
| Average | 1 | 2 | 3 | 5.6 | 7.8 | 4 | 9.2 | 5.8 | 6.8 | 9.8 |

*Rating Scale - 1 = lowest color density, 10 = highest color density

5. The method of claim 1 wherein organic liquid comprises one or more chemicals selected from (meth)acrylic monomers and oligomers.

6. The method of claim 1 wherein the organic liquid comprises one or more chemicals selected from nitrocellulose, cellulose acetate proprionate, and cellulose acetate butyrate.

7. The method of claim 1 wherein the organic liquid comprises ethyl acetate, butyl acetate, and nitrocellulose.

8. The method of claim 1 wherein the organic liquid comprises nitrocellulose, and one or more solvents selected from the group consisting of from butyl acetate, ethyl acetate, isopropanol, xylene, toluene, acetone, and methyl ethyl ketone.

9. The method of claim 1 wherein the organic liquid comprises ethyl acetate, isopropyl alcohol, and nitrocellulose.

10. The method of claim 1 wherein the gel composition comprises a mono-, di-, tri-, or tetra-functional acrylic or methacrylic monomer.

11. The method of claim 1 wherein the gel composition comprises a polyfunctional polyurethane (meth)acrylate oligomer.

12. The method of claim 1 wherein the gel composition comprises monomer selected from hydroxyethyl (meth)acrylate, hydroxypropyl (meth)acrylate, trimethylolpropane tri (meth)acrylate, and isobornyl (meth)acrylate.

13. The method of claim 1 wherein the gel composition comprises aliphatic polyester polyol based urethane diacrylate oligomer.

14. The method of claim 1 wherein the radiation-curable nail gel composition has a viscosity of below 25 poise.

15. The method of claim 1 wherein the radiation-curable nail gel composition and the pigment concentrate are packaged separately.

16. A method of adorning natural or artificial nails comprising applying a composition prepared by the method of claim 1 to a fingernail or toenail followed by curing under UV light.

17. The method of claim 1 wherein the ratio by weight of pigment concentrate to radiation-curable nail gel composition is equal to or less than 1:2.

18. A colored ultraviolet (UV) curable composition prepared by the process of claim 1.

19. A coating for a natural or artificial nail prepared by curing under actinic radiation a composition of claim 18.

* * * * *